United States Patent [19]

Hanson

[11] Patent Number: 5,630,716
[45] Date of Patent: May 20, 1997

[54] SELF-LIGATING ORTHODONTIC BRACKETS

[76] Inventor: G. Herbert Hanson, 57 Augusta Street, Hamilton, Ontario, Canada, L8N 1P8

[21] Appl. No.: 587,802

[22] Filed: Dec. 29, 1995

[51] Int. Cl.⁶ ..................................................... A61C 3/00
[52] U.S. Cl. ......................................... 433/14; 433/11
[58] Field of Search ............................ 433/10, 11, 13, 433/14, 15

[56] References Cited

U.S. PATENT DOCUMENTS

| | | | |
|---|---|---|---|
| 3,772,787 | 11/1973 | Hanson | 32/14 |
| 4,144,642 | 3/1979 | Wallshein | 433/11 |
| 4,248,588 | 2/1981 | Hanson | 433/11 |
| 4,355,975 | 10/1982 | Fujita | 433/11 |
| 4,386,909 | 6/1983 | Hanson | 433/20 |
| 4,492,573 | 1/1985 | Hanson | 433/11 |
| 4,698,017 | 10/1987 | Hanson | 433/11 |
| 4,712,999 | 12/1987 | Rosenberg | 433/13 X |
| 5,184,954 | 2/1993 | Hanson | 433/18 |
| 5,224,858 | 7/1993 | Hanson | 433/10 |
| 5,344,315 | 9/1994 | Hanson | 433/20 |
| 5,380,197 | 1/1995 | Hanson | 433/22 |
| 5,474,445 | 12/1995 | Voudouris | 433/11 X |

Primary Examiner—Nicholas D. Lucchesi
Attorney, Agent, or Firm—Rogers & Scott

[57] ABSTRACT

A self ligating orthodontic bracket comprising a U-shaped ligating spring member movable between slot open and closed positions on the bracket body is adapted for reception of an additional external ligating member, such as an elastomeric hoop or loop, by providing the spring member in its occlusal portion at least adjacent its junction with the lingual portion with a mesial distal extending spring slot in which the additional ligature is received and securely retained, the slot opening at least partly lingually and being convex in the labial gingival direction; preferably the slot opens both occlusally and lingually. Preferably also the gingival surface of the bracket body is provided with a mesial distal extending gingivally-opening body slot, convex in the occlusal direction, for reception and retention of an external additional ligating wire or elastomeric hoop engaged in the spring slot. Further, the mesial and distal surfaces of the bracket body are provided with respective grooves that cooperate with the slots for reception and retention of the additional ligating wire or hoop; the slots and grooves together may form a headed post for retention on the bracket of additional orthodontic elements such as a traction spring or a small hoop providing braking against sliding of the bracket along the wire.

29 Claims, 2 Drawing Sheets

SELF-LIGATING ORTHODONTIC BRACKETS

FIELD OF THE INVENTION

This invention is concerned with improvements in or relating to self-ligating orthodontic brackets, namely orthodontic brackets which comprise ligating spring means as an integral part thereof.

REVIEW OF THE PRIOR ART

The majority of orthodontic procedures employ a plurality of brackets that are attached to respective teeth, usually by cementing them to the teeth, together with an arch wire, so called because it is preformed to an optimum arch shape corresponding to the desired conformation of the teeth at the conclusion of the procedure. Arch wires of progressively increasing stiffness are used one at a time, the selected wire being engaged in mesial distal extending slots in the respective brackets and attached to the brackets by respective ligating means. When these procedures were first introduced the ligating means usually were metal wires that were twisted about the bracket and the arch wire; subsequently now that elastomeric materials have been developed suitable for the hostile environment of the human mouth elastic hoops or O-rings are increasingly commonly used. In another line of development each bracket comprises its own self-ligating metal spring member permanently mounted on the bracket body for movement between slot open and slot closed positions; specific examples of such self ligating brackets are those disclosed and claimed in my prior U.S. Pat. Nos. 3,772,787; 4,248,588 and 4,492,573, and in my prior application Ser. No. 08/274,077, filed 12 Jul. 1994, the disclosures of which are incorporated herein by this reference. These brackets are currently used by orthodontists in what is known as the Hanson SPEED System (Trade Mark) and have proven to be very successful.

One problem encountered with self-ligating brackets results from the extremely small size of the brackets and therefore of the metal springs. Because of the requirement for high modulus metals, and the highly corrodible environment of the mouth, it is necessary to use stainless steels. Although stainless steels of the highest practical modulus are used the tiny springs are stressed very close to the elastic limit as they are moved between the slot open and closed positions, and the amount of additional displacement required to exceed the limit is relatively small. Once the limit has been exceeded, for example by the operative carelessly moving the spring or attempting to force the spring to close over a stiff arch wire protruding too far out of the slot, then it may no longer function as a spring. This may require the bracket to be replaced completely, since it is not usually possible to replace the spring "in situs", and such replacement would of course be inconvenient and unpleasant both for the patient and the orthodontist.

A family of new nickel-titanium alloys has been developed, the most important characteristic of which is their extraordinarily high elasticity with corresponding resistance to overstressing and permanent deformation, as compared for example to the stainless steels. Their elasticity is such that ligating springs made from them are not overstressed when subjected to strains of as high as about 7.5%, as compared to the maximum for stainless steels of about 0.5%; they are commonly referred to as super-elastic shape memory alloys. With such high values it is highly unlikely that anything short of a catastrophic event could overstress the ligating springs. The new superelastic alloys are also used to produce arch wires that can be bent to an extraordinary degree out of their arch shape without permanent deformation to engage them in the bracket slots, and an example of such a multi-strand wire is that disclosed and claimed in my prior U.S. Pat. No. 5,344,315, issued 6 Sep. 1994, the disclosure of which is incorporated herein by this reference.

Another problem that arises is that it may not be possible to engage an arch wire of the selected stiffness in the slot of one or more of the brackets, and at the same time move the ligating spring to the slot closed position, without bending the wire to such a degree that it would apply unacceptably high forces to the tooth, and/or that it would take a permanent set, thereby stopping it from producing correctional movement of the brackets and teeth. The problem will rarely arise if superelastic alloy wires are used, but they are more expensive and stainless steels will continue to be used. A solution has been to allow the wire to protrude at least partly, and sometimes completely, out of the slot, despite the adverse effect this can have on interarch dimensional coordination, and to attach it to the bracket body by means of a wire or thread passed through a supplementary bore or slot in the body, until enough tooth movement has taken place for the wire to engage in the slot sufficiently for the ligating spring to be moved to the closed position. Cases may still be encountered in which even superelastic wires cannot be bent sufficiently and an external ligature must be employed.

An important consideration is that orthodontists who have been using external elastomeric hoop ligatures in their procedures, and are therefore thoroughly familiar with their characteristics, may be reluctant initially to adopt a completely new procedure such as is required by adoption of self-ligating brackets, unless it permits them at least the opportunity of using their established skill and experience in this regard, and would therefore be reassured if provided with a self ligating bracket that also had positive provision for the use of an external hoop ligature whenever the orthodontist felt it appropriate to do so.

A surprising important further consideration is that many child patients are requesting "colored braces like their friends have". What they are really referring to are the elastomeric hoop ligatures used in the other procedures which are changed at each appointment, and which are now available in a variety of colors, so that the child can even at each visit request a new color to suit the season or occasion, e.g. black at halloween and red at Christmas. Orthodontic procedures are inherently somewhat stressful for child patients and anything that can help reduce that stress is welcome.

SUMMARY OF THE INVENTION

It is a principal object of the invention therefore to provide new self-ligating brackets that can be used in combination with external ligating means, such as a ligating hoop of elastomeric material, in circumstances that such use is needed, preferred or desired.

In accordance with the invention there is provided an orthodontic bracket comprising:

a bracket body having labial, lingual, gingival, occlusal, mesial and distal surface portions, the body having a mesial distal extending arch wire slot opening to the labial surface portion; and a generally U-shaped ligating spring member of thin resilient material having labial and lingual portions connected by an intervening occlusal portion and being movable on the body between two positions in which the slot opening is respectively open and is closed by the spring member lingual portion;

wherein the spring member is provided in the occlusal portion, at or adjacent to its junction with the lingual portion, with a mesial distal extending spring member slot for reception and retention of an additional ligating means, the spring member slot opening at least partly lingually and being convex in the labial gingival direction.

Preferably the spring slot opens both occlusally and lingually.

Preferably also the gingival surface of the bracket body is provided with a mesial distal extending gingival-opening body slot convex in the occlusal direction for reception and retention of an external additional ligating means mounted on the bracket and engaged in the spring member slot.

The mesial and distal surfaces of the bracket body preferably are provided with respective gingivally occlusally extending grooves also for reception of an additional ligating means mounted on the bracket and engaged in the spring member slot.

DESCRIPTION OF THE DRAWINGS

Particular preferred embodiments of the invention will now be described, by way of example, with reference to the accompanying diagrammatic drawings, wherein.

DESCRIPTION OF THE PREFERRED EMBODIMENTS

For convenience and simplicity in description the embodiments are illustrated and described herein and claimed in the appended claims as they would be used in the lower central incisor region of a patient's mouth and in the conventional so-called labial technique, in which the brackets are attached to the labial surfaces of the teeth. The brackets of the invention are equally usable in the so-called lingual technique, in which they are attached to the teeth lingual surfaces so that they are concealed from view as much as possible; however when so used the slot opens to the lingual and not the labial, and the gingival and occlusal directions may also be reversed. Again for convenience in description the brackets are described as having specific named surfaces but, as is well known to those skilled in this art, it is usual in their manufacture wherever possible to avoid sharp edge junctions between the various surfaces, and they therefore usually merge smoothly with one another without a definite junction between them being apparent.

Figure 1:
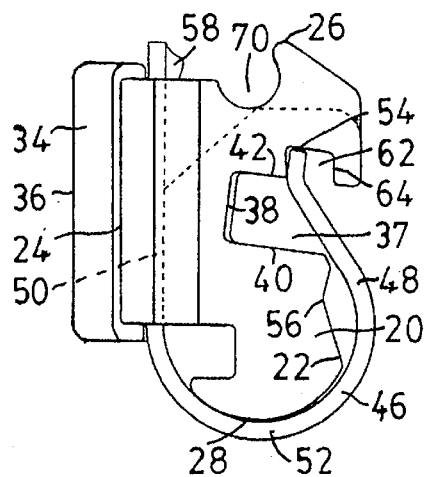
FIG. 1 is a side elevation of a prior art Hanson SPEED system bracket.

My prior art bracket Hanson SPEED System shown in FIG. 1, and each bracket of the present invention shown in FIGS. 2, 3 and 6–10 consists of a bracket body 20 having labial, lingual, gingival, occlusal, mesial and distal surfaces 22, 24, 26, 28, 30 and 32 respectively. Such a bracket is mounted on a respective tooth (not shown), either by attaching it to a tooth-embracing band (not shown), or by cementing it directly to the tooth. When the bracket is to be attached by cement the body lingual surface 24 has a cementing pad 34 attached thereto, which in turn provides a lingual surface 36 that is applied to the tooth labial surface. Such brackets are employed by attaching each to its respective tooth in an attitude such that, as each arch wire attempts to return to its preformed arch shape, the tooth is moved toward its desired optimized position and attitude. There are two principal methods to achieve this, in the first of which all of the torque requirements (rotation about a mesial distal axis), angulation requirements (rotation about a labial lingual axis), and first order pre-adjustments, are obtained by suitable shaping of the bracket bases, particularly of their lingual surfaces and variation of their thicknesses, so that all of the labial faces are aligned when the teeth are in their optimum attitude and rotational position. In the second method the bases are all approximately of the same shape and thickness and the necessary adjustment is obtained by varying the angulation of the arch wire receiving slot about a mesial distal extending axis. A combination of the two methods can also be employed to avoid excessive size of the bracket bases and to avoid excessive angulation of the slots.

All of the embodiments shown are provided with a rectangular gingival-occlusal transverse cross section, mesial-distal extending arch wire slot 37 opening to the labial surface 22 and having lingual, gingival and occlusal surfaces 38, 40 and 42 respectively. The slot receives a succession of arch wires 44, which usually in the early stages of a procedure are of circular cross section as shown; subsequently a succession of wires of rectangular cross section usually is used for final control of tipping of the teeth into position. Arch wire slots of other than rectangular cross section and cooperating arch wires of other than round and rectangular cross section can also be used in the brackets of the invention, for example those shown in my U.S. Pat. No. 4,386,909, the disclosure of which is incorporated herein by this reference.

Means for retaining the arch wire in the slot, and for pressing it lingually into engagement with the slot lingual face 38, comprise a self-ligating spring member 46 of thin flat springy metal, and of U-shape with converging arms, referred to herein for convenience as generally U-shaped, the shape enabling it to tightly embrace the body 20 and to conform closely to the labial, occlusal and lingual faces thereof while in the slot closed position. For convenience in description this ligating retaining member may be regarded as comprising opposed labial and lingual portions 48 and 50 respectively, each in embracing sliding engagement with the respective bracket body surface, and a connecting occlusal portion 52. The member is movable in this sliding and embracing movement on the body between the slot closed position shown in solid line in FIGS. 2, 3 and 6–10 to the slot open position shown in broken line in FIG. 7; in the latter position free edge part 54 of the labial portion 48 engages on a parking land, consisting of a step 56 in the body labial surface, to retain the member in that position.

The lingual portion 50 moves freely but without play in a groove formed in the lingual face of the bracket body, the groove lingual side being closed to form an enclosing passage by the cementing pad 34. The portion 50 is relatively straight so as to guide the ligating member for corresponding straight gingival occlusal movement between the two positions, and is dimpled (or returned as shown in FIGS. 6–8 and 10) at 58 at its free end to prevent the member being moved beyond the slot open position off the bracket, and to provide an enlarged area for engagement by the end of an opening tool (not shown) applying a gingivally directed opening force in the direction of the arrow 60 in FIG. 7. A mesial distal extending, occlusal opening, spring member retaining slot 62 is provided immediately labially of the arch wire slot with its occlusal opening in the plane of the gingival surface of the arch wire slot. In the slot closed position the free labial end 54 of the ligating spring member enters the slot 62, the lingual wall 64 of which can be engaged by the end 54 when the wire is not fully engaged in the slot but is protruding labially out of it. The labial lingual dimension of this slot 62 is such that the retaining wall restricts any such labial movement of the spring ligating member labial portion to the maximum that is possible without overstressing and damaging it.

Figure 2:
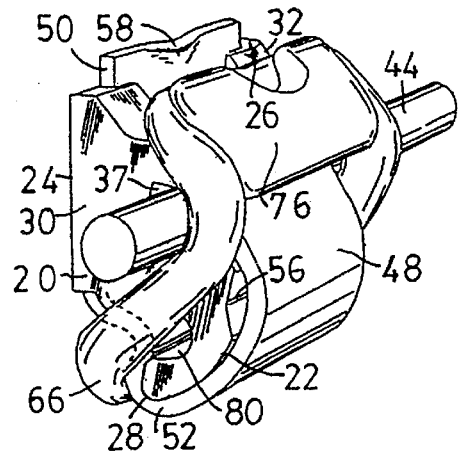
FIG. 2 is a perspective view from the labial of a bracket which is a first embodiment, shown with an arch wire in the arch wire slot, the ligating spring member in the slot closed position, and an additional elastomeric ligating hoop in position on the bracket body.
Figure 3:
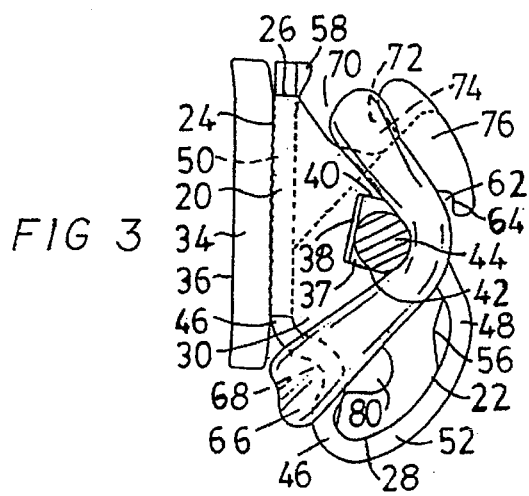
FIG. 3 is a side elevation from the mesial of the bracket of FIG. 2.
Figure 4:
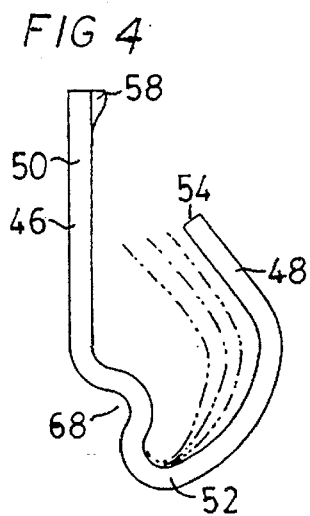
FIG. 4 is a side elevation of a ligating spring member showing in broken lines possible unconstrained conformations before it is mounted on the bracket body.

FIGS. 2 and 3 show the manner in which an additional elastomeric ligating hoop 66 is securely mounted on a bracket of the invention in the event that the procedure makes it desirable to employ such an element, or it is the preference of the orthodontist to employ it. The spring member 46 is provided at the junction of the occlusal portion 52 and the lingual portion 50 with a mesial distal extending spring member slot 68 for reception and retention of the additional ligating means 66, this spring slot opening both lingually and occlusally and being convex in the labial gingival direction. The slot 68 is deep enough to ensure secure retention of the hoop therein, with the constraint that deepening of the slot beyond the necessary amount will usually produce an undesired increase in the labial lingual dimension of the bracket body. The slot is provided in the occlusal portion at or adjacent to its junction with the lingual portion, and preferably, as shown, immediately at that junction. The slot must open at least partly lingually to perform its required function and in practice cannot open entirely occlusally since secure retention would not be obtained. A slot that opens completely lingually would function successfully, but would result in an increase in the gingival occlusal length of the bracket, whereas it is a constant endeavor with these brackets to make them as small as possible; the combined lingual occlusal opening of the spring member slot is therefore preferred.

Prior art brackets, such as that shown in FIG. 1, have been provided in their gingival surface with a mesial distal extending, gingivally opening, body slot 70 that is convex in the occlusal direction. Its purpose is that, in the event that the arch wire is so far displaced from the arch wire slot 37 that it cannot be engaged therein, or it protrudes so far out of the slot that the spring ligating member 46 cannot be moved to the slot closed position, a tie wire or an elastomeric thread can be passed through the slot 70 and used to secure the arch wire to the bracket until enough correction has taken place for the wire to be sufficiently inserted in the slot for the ligating spring member to be closed thereon. An elastomeric hoop or O-ring cannot be used, since they cannot be retained sufficiently securely. The bodies of the brackets of the invention are provided with such a gingivally-located slot 70 that is enlarged both occlusally and labially for secure reception and retention of the additional ligating hoop means 66 engaged in the spring slot 68, the wall of the slot being returned lingually and in the gingival direction to provide a pronounced generally U-shaped lingually-opening slot part 72 into which the ligature 66 fits snugly and securely as it is urged by its resilience in the labial direction.

Figure 8:
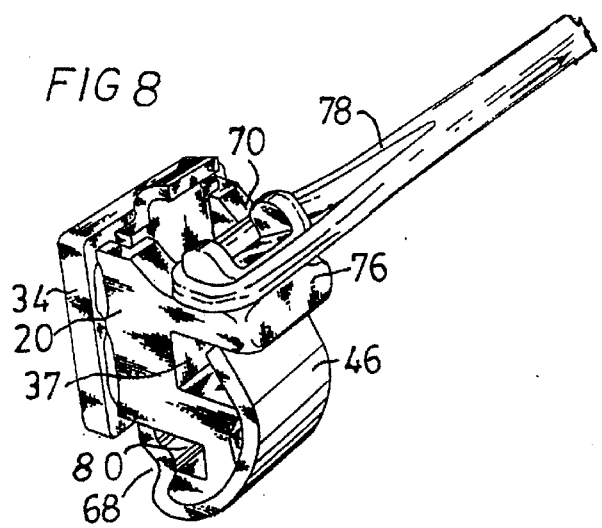
FIG. 8 is a perspective view of the bracket of FIG. 6 showing an elastomeric traction spring attached thereto.

In this embodiment the body is further provided in its mesial and distal surfaces with respective gingivally occlusally extending grooves 74 extending from slot part 70 to the occlusally-opening retaining slot 62, these grooves receiving the adjacent side parts of the hoop and assisting in its secure retention on the body. Such a slotted and grooved structure results in a gingivally-located body portion 76 having the shape of a mushroom headed post and usable as a tie wing that not only securely retains a hoop ligature 66, but can also serve as a secure attachment for an auxiliary device, such as an elastomeric tension spring 78, as shown in FIG. 8. Such springs are disclosed in more detail and claimed in my U.S. Pat. No. 5,184,954, issued 9th Feb. 1993, the disclosure of which is incorporated herein by this reference.

An example of when an additional elastomeric hoop ligature would be used with the self ligating brackets of the invention is the case where it is desired to inhibit mesial-distal sliding movement of a specific bracket or brackets along the arch wire. Hitherto this has been done by providing a stop on or in the wire against which the bracket butts so as to be prevented from such sliding, but as will be seen from FIGS. 2 and 3 the strong engagement of the hoop with the wire enables the additional ligature to act as an excellent resilient brake. Another example is the use in a strategic area to inhibit the wire from sliding mesially and possibly escaping from the terminal attachments by which the ends of the wire are secured to the teeth.

Figure 9:
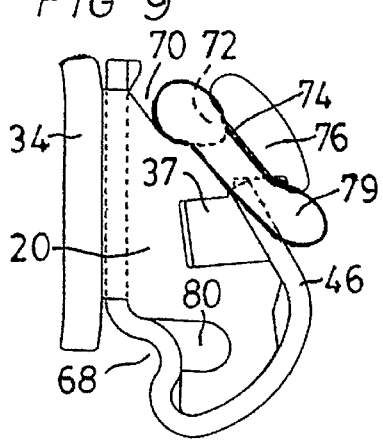
FIG. 9 is a side elevation similar to FIG. 3 showing the mounting of a small elastomeric hoop thereon.

The provision of the additional slot part 70 facilitates the use of another additional ligating means consisting of a small elastomeric hoop 79, shown in FIG. 9, that is just large enough to fit snugly around the tie wing body portion 76, in which position it also engages around the end of the ligating spring for greater security of its retention. Such an additional ligature can also provide a smaller controlled amount of braking against mesial distal sliding than is produced by the larger hoop ligature 66, by using it in conjunction with an arch wire that is large enough to be frictionally engaged by the main ligating spring 46, the urge of the additional ligature increasing the frictional contact between the wire and the spring.

Preferably the ligating springs 46 are fabricated from a member of the family of new nickel-titanium superelastic shape memory alloys referred to above and described and claimed in more detail in my prior application Ser. No. 08/274,077, filed Jul. 12, 1994, the disclosure of which is incorporated herein by this reference. The alloys produced to date are of lower strength modulus that the available stainless steels, and a spring member of equivalent strength must usually be made of somewhat thicker material, e.g. 0.178 mm (0.007 in) instead of 0.127 mm (0.005 in).

Figure 5:
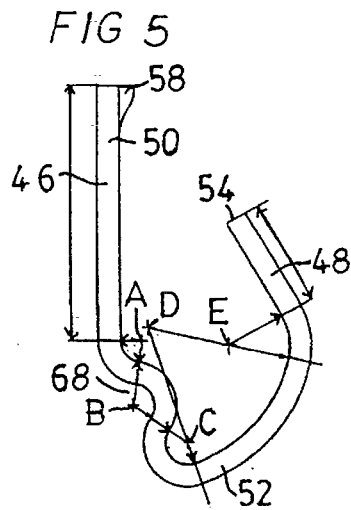
FIG. 5 is a side elevation of the ligating spring member of FIG. 4 in constrained conformation as mounted on the bracket body.
Figure 6:
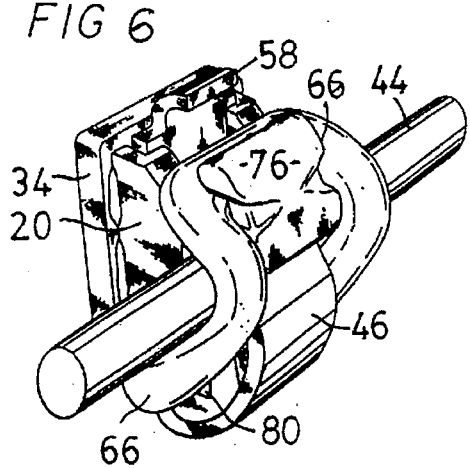
FIG. 6 is a perspective view from the labial, similar to FIG. 2, of a second embodiment.

FIG. 5 shows in solid line the conformation of a ligating spring member 46 when mounted on a bracket in the slot closed position, and in broken lines the various alternative unconstrained configurations in which the member can be formed and set by appropriate heat treatment; as the free end of the labial portion is moved closer to the lingual portion the force with which the member embraces the body, and the force applied by the member to an arch wire, are increased to provide a corresponding increase in the torquing capability of the bracket. FIG. 6 shows the mesial or distal profile of the spring member when in position on the bracket body in slot closed position, the occlusal gingival cross section of the bracket body being such that the spring profile has no abrupt bends. Thus, the lingual portion 50 is straight along its entire length (except for the dimple 58) and its junction part with the occlusal portion is smoothly curved about a radius point A; the junction part blends smoothly with the slotted part 68, which is smoothly curved about a radius point B; the slotted part blends smoothly with the two smoothly blended successive parts of the occlusal portion 52, these two parts being smoothly curved about respective radius points C and D; the labial portion comprises two parts that blend smoothly with the occlusal part and with one another, the part at the junction with the occlusal portion being smoothly curved about radius point E, while the remaining part is straight.

It is found surprisingly that with the new ligating spring configurations of the invention it is possible to reduce the labial lingual dimension of the bracket body, in the case of the specific examples by 0.2 mm (0.008 in), despite the additional spring thickness required when superelastic alloys are used; every decrease, even such a small one, is desirable in this particular field in view of the importance attached to minimisation of size by both patients and orthodontists. Advantage is taken of the smaller possibility of overstressing with these alloys to make the labial portion 48 of the spring member of the invention with a longer radius about radius point D (compare FIGS. 1 and 5), despite the much smaller radius that is then required about radius point C, so that this portion of the spring member is somewhat less protuberant, especially toward the occlusal, and this is particularly important in that it is predominantly this surface that is engaged by the patient's lips.

As shown in FIG. 1, my prior art brackets are usually provided with an additional mesial distal extending, lingually-opening, occlusally-located slot 80. This slot may also be used, as with the slot 70, for reception and retention of the prior art tie wire or elastomeric thread referred to above, and further for the attachment of supplementary orthodontic elements to the bracket, including the reception of a portion of a second arch wire supplementing the action of the primary arch wire. The slot is located in the lingual surface portion of the bracket at its junction with the occlusal portion, and usually is also of rectangular gingival occlusal transverse cross section. Although the slot is open to the lingual surface portion it is effectively always closed by the ligating spring member 46, so that the tie wire or elastomeric thread must be passed through it and the simpler, faster and more effective closed elastomeric hoops cannot be used. Preferably, in the brackets of the invention the bracket body is also provided with such a mesial distal extending, lingually-opening, occlusally-located body slot 80, which is located in the body at a position such that the slotted part of the spring member 46 protrudes therein when the spring member is in the slot closed position, thereby facilitating minimization of the labial lingual dimension of the bracket body. The slot 80 is still able to receive a tie wire or an elastomeric thread, if required, although that function is now much more readily and effectively provided by the elastomeric hoop ligature 66, and it is of greater labial extent than the slot in the prior art brackets, so that it can accommodate both such an additional tie wire or thread and the adjacent slotted portion of the spring. In this embodiment the labial surface of the slot 80 is of semi-circular transverse cross section to avoid the presence of abrupt junctions so close to the bracket body labial surface; a slot or recess of this cross sectional shape is suitable for use with round cross section arch wires, in the event that such a supplementary arch wire is to be used, and also with D-shape cross section arch wires, as disclosed for example in my U.S. Pat. Nos. 4,698,017, 5,224,858, 5,344,315 and 5,380,197, the disclosures of which are incorporated herein by this reference.

Figure 10:
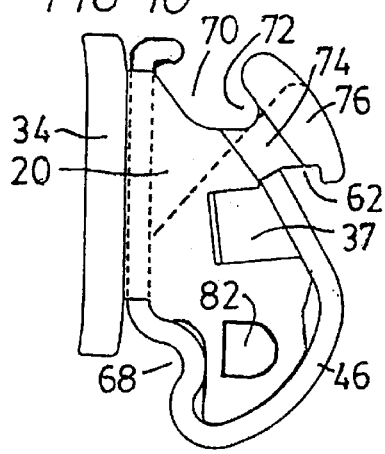
FIG. 10 is a side elevation similar to FIG. 3 of a third embodiment.

FIG. 10 shows an embodiment in which, in order to ensure adequate strength at the occlusal end of the bracket body, only a shallow slot 80 is provided, just sufficient to accommodate the slotted portion 68 of the spring member, while a separate D-shape transverse cross section mesially distally extending bore 82 is provided in place of the deep slot 80 of the other embodiments.

Figure 7:
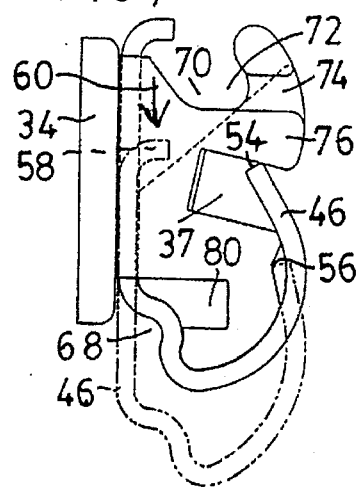
FIG. 7 is a side elevation of the embodiment of FIG. 6 with the arch wire and elastomeric ligating hoop removed.

In the embodiments of FIGS. 6–8 the occlusally-opening slot 62 and the retaining wall 64 are eliminated and the grooves 74 extend from the slot part 72 directly to the gingival surface 40 of the arch wire slot 37 and the bracket body labial surface 22. Such brackets are used, for example, on the upper central incisors where escape of the arch wire from its slot is unlikely, but where there is danger of a rectangular cross section arch wire rotating about a mesial distal axis into the slot 62, if provided, so that the wire is not able to perform its required function of rotating the bracket and the attached tooth about a mesial distal axis.

I claim:

1. An orthodontic bracket comprising:
   a bracket body having labial, lingual, gingival, occlusal, mesial and distal surface portions, the body having a mesial distal extending arch wire slot opening to the labial surface portion; and
   a generally U-shaped ligating spring member having labial and lingual portions connected by an intervening occlusal portion and being movable on the body between two positions in which the slot labial opening is respectively open and is closed by the labial portion;
   wherein the spring member is provided in the occlusal portion adjacent to its junction with the lingual portion with a mesial distal extending spring member slot that in the slot closed position is available to receive and retain an additional ligating means mounted on the bracket, and that is deep enough for such reception and retention, the spring member slot opening at least partly lingually and being convex in the labial gingival direction.

2. A bracket as claimed in claim 1, wherein the spring member slot opens both occlusally and lingually.

3. A bracket as claimed in claim 1, wherein the lingual surface of the bracket body is provided with a mesial distal extending, lingually-opening, occlusally-located body slot into which the part of the spring member having the spring member slot protrudes when the spring member is in the slot closed position.

4. A bracket as claimed in claim 1, wherein the bracket body is provided at its occlusal end with a mesially distally extending bore for passage of an orthodontic element to be mounted on the bracket.

5. A bracket as claimed in claim 1, wherein the gingival surface portion of the bracket body is provided with a mesial distal extending, gingivally-opening ligating means receiving body slot for reception and retention of an external additional ligating means mounted on the bracket and engaged in the spring member slot.

6. A bracket as claimed in claim 5, wherein the ligating means receiving body slot also extends in the labial direction to provide a slot portion of U-shape transverse cross section into which an additional ligating means mounted on the bracket can engage.

7. A bracket as claimed in claim 5, wherein the arch wire slot is provided adjacent its junction with the bracket body labial face portion with a mesially distally extending, occlusally-opening spring member retaining slot parallel to the ligating means receiving body slot, the portion of the bracket body between the two last-mentioned slots constituting a tie wing for retention on the bracket of additional orthodontic elements.

8. A bracket as claimed in claim 5, wherein the arch wire slot is provided adjacent its junction with the bracket body labial face portion with a mesially distally extending, occlusally-opening spring member retaining slot parallel to the ligating means receiving body slot, and the mesial and distal surface portions of the bracket body are provided with respective gingivally occlusally extending grooves extending between the spring member retaining slot and the ligating means receiving slot, the last-mentioned two slots and the grooves cooperating for retention on the bracket of additional orthodontic elements mounted on the bracket.

9. A bracket as claimed in claim 8, wherein the gingivally-opening body slot also extends in the labial direction to provide a slot portion of U-shape transverse cross section into which an additional ligating means mounted on the bracket can engage, the portion of the bracket body between the spring member retaining slot, the ligating means receiving slot and the grooves having the shape of a headed post for attachment of an auxiliary orthodontic device.

10. A bracket as claimed in claim 1, wherein the mesial and distal surfaces of the bracket body are provided with respective gingivally occlusally extending grooves for reception of an additional ligating means mounted on the bracket and engaged in the spring member slot.

11. An orthodontic bracket comprising:
   a bracket body having labial, lingual, gingival, occlusal, mesial and distal surface portions, the body having a mesial distal extending arch wire slot opening to the labial surface portion; and
   a generally U-shaped ligating spring member having labial and lingual portions connected by an intervening occlusal portion and being movable on the body between two positions in which the slot labial opening is respectively open and is closed by the labial portion;
   wherein the spring member is provided in the occlusal portion adjacent to its junction with the lingual portion with a mesial distal extending spring member slot that in the slot closed position is available to receive and retain an additional ligating means mounted on the bracket, and that is deep enough for such reception and retention, the spring member slot opening at least partly lingually and being convex in the labial gingival direction;
   wherein the lingual surface portion of the bracket body is provided with a mesial distal extending, lingually-opening, occlusally-located body slot into which the part of the spring member having the spring member slot protrudes when the spring member is in the slot closed position; and
   wherein the gingival surface portion of the bracket body is provided with a mesial distal extending, gingivally-opening ligating means receiving body slot for reception and retention of an external additional ligating the bracket and engaged in the spring member slot.

12. A bracket as claimed in claim 11, wherein the ligating means receiving body slot also extends in the labial direction to provide a slot portion of U-shape transverse cross section into which an additional ligating means mounted on the bracket can engage.

13. A bracket as claimed in claim 11, wherein the arch wire slot is provided adjacent its junction with the bracket body labial surface portion with a mesially distally extending, occlusally-opening spring member retaining slot parallel to the ligating means receiving body slot, the portion of the bracket body between the two last-mentioned slots constituting a tie wing for retention on the bracket of additional orthodontic elements.

14. A bracket as claimed in claim 11, wherein the arch wire slot is provided adjacent its junction with the bracket body labial surface portion with a mesially distally extending, occlusally-opening spring member retaining slot parallel to the ligating means receiving body slot, and the mesial and distal surface portions of the bracket body are provided with respective gingivally occlusally extending grooves extending between the spring member retaining slot and the ligating means receiving slot, the last-mentioned two slots and the grooves cooperating for retention on the bracket of additional orthodontic elements mounted on the bracket.

15. A bracket as claimed in claim 14, wherein the gingivally-opening body slot also extends in the labial direction to provide a slot portion of U-shape transverse cross section into which an additional ligating means mounted on the bracket can engage, the portion of the bracket body between the spring member retaining slot, the ligating means receiving slot and the grooves having the shape of a headed post for attachment of an auxiliary orthodontic device.

16. An orthodontic bracket comprising:
   a bracket body having labial, lingual, gingival, occlusal, mesial and distal surface portions, the body having a mesial distal extending arch wire slot opening to the labial surface portion; and
   a generally U-shaped ligating spring member having labial and lingual portions connected by an intervening occlusal portion and being movable on the body between two positions in which the slot labial opening is respectively open and is closed by the labial portion;
   wherein the spring member is provided at the junction of the occlusal portion with the lingual portion with a mesial distal extending spring member slot that in the slot closed position is available to receive and retain an additional ligating means mounted on the bracket, and that is deep enough for such reception and retention, the spring member slot opening both occlusally and lingually and being convex in the labial gingival direction.

17. A bracket as claimed in claim 16, wherein the lingual surface of the bracket body is provided with a mesial distal extending, lingually-opening, occlusally-located body slot into which the part of the spring member having the spring member slot protrudes when the spring member is in the slot closed position.

18. A bracket as claimed in claim 16, wherein the bracket body is provided at its occlusal end with a mesially distally extending bore for passage of an orthodontic element to be mounted on the bracket.

19. A bracket as claimed in claim 16, wherein the gingival surface portion of the bracket body is provided with a mesial distal extending, gingivally-opening ligating means receiving body slot for reception and retention of an external additional ligating means mounted on the bracket and engaged in the spring member slot.

20. A bracket as claimed in claim 19, wherein the ligating means receiving body slot also extends in the labial direction to provide a slot portion of U-shape transverse cross section into which an additional ligating means mounted on the bracket can engage.

21. A bracket as claimed in claim 19, wherein the arch wire slot is provided adjacent its junction with the bracket body labial surface portion with a mesially distally extending, occlusally-opening spring member retaining slot parallel to the ligating means receiving body slot, the portion of the bracket body between the two last-mentioned slots constituting a tie wing for retention on the bracket of additional orthodontic elements.

22. A bracket as claimed in claim 19, wherein the arch wire slot is provided adjacent its junction with the bracket body labial surface portion with a mesially distally extending, occlusally-opening spring member retaining slot parallel to the ligating means receiving body slot and the mesial and distal surface portions of the bracket body are provided with respective gingivally occlusally extending grooves extending between the spring member retaining slot and the ligating means receiving slot, the last-mentioned two slots and the grooves cooperating for retention on the bracket of additional orthodontic elements mounted on the bracket.

23. A bracket as claimed in claim 22, wherein the gingivally-opening body slot also extends in the labial direction to provide a slot portion of U-shape transverse cross section into which an additional ligating means mounted on the bracket can engage, the portion of the bracket body between the spring member retaining slot, the ligating means receiving slot and the grooves having the shape of a headed post for attachment of an auxiliary orthodontic device.

24. A bracket as claimed in claim 16, wherein the mesial and distal surfaces of the bracket body are provided with respective gingivally occlusally extending grooves for reception of an additional ligating means mounted on the bracket and engaged in the spring member slot.

25. An orthodontic bracket comprising:

a bracket body having labial, lingual, gingival, occlusal, mesial and distal surface portions, the body having a mesial distal extending arch wire slot opening to the labial surface portion; and a generally U-shaped ligating spring member having labial and lingual portions connected by an intervening occlusal portion and being movable on the body between two positions in which the slot labial opening is respectively open and is closed by the labial portion;

wherein the spring member is provided at the junction of the occlusal portion with the lingual portion with a mesial distal extending spring member slot that in the slot closed position is available to receive and retain an additional ligating means mounted on the bracket, and that is deep enough for such reception and retention, the spring member slot opening both occlusally and lingually and being convex in the labial gingival direction;

wherein the lingual surface portion of the bracket body is provided with a mesial distal extending, lingually-opening, occlusally-located body slot into which the part of the spring member having the spring member slot protrudes when the spring member is in the slot closed position; and wherein the gingival surface portion of the bracket body is provided with a mesial distal extending, gingivally-opening ligating means receiving body slot for reception and retention of an external additional ligating means mounted on the bracket and engaged in the spring member slot.

26. A bracket as claimed in claim 25, wherein the ligating means receiving body slot also extends in the labial direction to provide a slot portion of U-shape transverse cross section into which an additional ligating means mounted on the bracket can engage.

27. A bracket as claimed in claim 25, wherein the arch wire slot is provided adjacent its junction with the bracket body labial face portion with a mesially distally extending, occlusally-opening spring member retaining slot parallel to the ligating means receiving body slot, the portion of the bracket body between the two last-mentioned slots constituting a tie wing for retention on the bracket of additional orthodontic elements.

28. A bracket as claimed in claim 25, wherein the arch wire slot is provided adjacent its junction with the bracket body labial face portion with a mesially distally extending, occlusally-opening spring member retaining slot parallel to the ligating means receiving body slot, and the mesial and distal surface portions of the bracket body are provided with respective gingivally occlusally extending grooves extending between the spring member retaining slot and the ligating means receiving slot, the last-mentioned two slots and the grooves cooperating for retention on the bracket of additional orthodontic elements mounted on the bracket.

29. A bracket as claimed in claim 28, wherein the gingivally-opening body slot also extends in the labial direction to provide a slot portion of U-shape transverse cross section into which an additional ligating means mounted on the bracket can engage, the portion of the bracket body between the spring member retaining slot, the ligating means receiving slot and the grooves having the shape of a headed post for attachment of an auxiliary orthodontic device.

* * * * *